US012636508B2

(12) United States Patent
Moore et al.

(10) Patent No.: US 12,636,508 B2
(45) Date of Patent: May 26, 2026

(54) WEARABLE MEDICAL SYSTEM WITH DEVICE PARAMETERS AND PATIENT INFORMATION PROGRAMMABLE VIA BROWSER INTERFACE

(71) Applicant: West Affum Holdings DAC, Dublin (IE)

(72) Inventors: Mark P. Moore, Redmond, WA (US); David P. Finch, Bothell, WA (US)

(73) Assignee: West Affum Holdings Dublin DAC, Dublin (IE)

( * ) Notice: Subject to any disclaimer, the term of this patent is extended or adjusted under 35 U.S.C. 154(b) by 613 days.

(21) Appl. No.: 18/063,457

(22) Filed: Dec. 8, 2022

(65) Prior Publication Data

US 2023/0381527 A1     Nov. 30, 2023

Related U.S. Application Data

(60) Provisional application No. 63/347,463, filed on May 31, 2022.

(51) Int. Cl.
*A61N 1/39* (2006.01)
*A61N 1/04* (2006.01)
*A61N 1/372* (2006.01)

(52) U.S. Cl.
CPC ......... *A61N 1/3904* (2017.08); *A61N 1/0484* (2013.01); *A61N 1/37252* (2013.01); *A61N 1/3993* (2013.01)

(58) Field of Classification Search
CPC .. A61N 1/046; A61N 1/0484; A61N 1/37252; A61N 1/3904; A61N 1/3925; A61N 1/3993; G16H 40/40; G16H 40/67
See application file for complete search history.

(56) References Cited

U.S. PATENT DOCUMENTS 3,724,355 A    4/1973   Busch et al.
3,724,455 A    4/1973   Unger
(Continued)

FOREIGN PATENT DOCUMENTS

DE        2005060985 A2    6/2007
EP           2305110 A1    4/2011
(Continued)

OTHER PUBLICATIONS

Extended European Search Report received on Jul. 8, 2023 for EP Application No. 23174868; 14 pages total.
Search Report for Japanese Application No. 2023-006950 dated Jul. 30, 2024, 27 Pages (12 Pages of Official Copy and 15 Pages of English Translation).
Notice of refusal for Japanese Application No. 2023-006950 dated Aug. 20, 2024, 11 Pages (6 Pages of Official Copy and 5 Pages of English Translation).
(Continued)

*Primary Examiner* — Amanda K Hulbert
(74) *Attorney, Agent, or Firm* — Seed Intellectual Property Law Group LLP

(57)                ABSTRACT

A wearable monitoring device system includes a wearable monitoring device (WMD), including a support structure and a plurality of electrodes. A WMD data store includes parameter data that define settings of the WMD, interpreted code that provides access to the parameter data, a web server configured to serve the interpreted code. The WMD includes a WMD processor configured to execute the web server. The system includes a companion device communicatively coupled to the WMD, including a display, a companion communication module configured to communicatively couple the companion device and the WMD, and a companion data store. The companion data store includes a browser configured to render the interpreted code. A companion processor is included, configured to execute the browser.

16 Claims, 8 Drawing Sheets

(56) References Cited

U.S. PATENT DOCUMENTS

| | | | |
|---|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,460,834 B2 | 10/2019 | Johnson |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0109904 A1 | 6/2003 | Silver |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0091175 A1 | 4/2008 | Frikart et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0174620 A1 | 6/2016 | Weast et al. |
| 2016/0256104 A1 | 9/2016 | Romem et al. |
| 2016/0283900 A1 | 9/2016 | Johnson et al. |
| 2016/0296114 A1 | 10/2016 | Finch |
| 2017/0007129 A1 | 1/2017 | Kaib et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |

(56) References Cited

U.S. PATENT DOCUMENTS

| | | | |
|---|---|---|---|
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030351 A1 | 1/2019 | Sullivan et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2021/0361957 A1* | 11/2021 | Kaib | G16H 80/00 |
| 2022/0313161 A1* | 10/2022 | Shahandeh | A61B 5/0022 |

FOREIGN PATENT DOCUMENTS

| | | |
|---|---|---|
| JP | 4320257 A | 3/2005 |
| JP | 2008-538708 A | 11/2008 |
| JP | 5963767 B | 1/2014 |
| JP | 2014526282 A | 10/2014 |
| JP | 2015-510780 A | 4/2015 |
| JP | 2018-503168 A | 2/2018 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

Examination Report received on Jan. 26, 2026 for EP Application No. 23174868; 12 pages.

* cited by examiner

*Components of External Defibrillator*

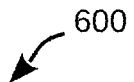
600

| Subject | Identity of the Certificate Holder |
|---|---|
| Issuer | Identity of Certifying Authority |
| Expiration | Date after which digital certificate is no longer valid |
| Public Key | Public Key of the Certificate Holder |
| Algorithm | Hashing algorithm used to sign the digital certificate |
| Unique Identifier | Value that uniquely identifies the digital certificate |

| Permissions | Tasks that Certificate Holder is authorized to perform |
|---|---|
| Other Data | Arbitrary or structured data may be verified or trusted |

| Signature | Signature of the Certifying Authority created using Certifying Authority's private key |
|---|---|

*Fig. 6*

WEARABLE MEDICAL SYSTEM WITH DEVICE PARAMETERS AND PATIENT INFORMATION PROGRAMMABLE VIA BROWSER INTERFACE

CROSS-REFERENCE TO RELATED APPLICATION

The present application claims priority to and the benefit of Provisional Application No. 63/347,463, filed May 31, 2022, the entire disclosure of which is hereby incorporated by reference herein in its entirety for all purposes.

SUMMARY OF THE DISCLOSURE WITH BACKGROUND

When people suffer from some types of heart arrhythmias, the result may be that blood flow to various parts of the body is reduced. Some arrhythmias may even result in Sudden Cardiac Arrest (SCA). SCA can lead to death very quickly unless treated, e.g., within 10 minutes. Some observers mistake SCA for a heart attack, which it is not.

Some people have an increased risk of SCA. Such people include patients who have had a heart attack or a prior SCA episode. A frequent recommendation for these people is to receive an Implantable Cardioverter Defibrillator (ICD). The ICD is surgically implanted in the chest, and continuously monitors the patient's electrical activity. If certain heart arrhythmias are detected, the ICD delivers an electric shock directly to the heart in an attempt to correct the arrhythmia.

As a further precaution, people who have been identified with an increased risk of SCA are sometimes given a Wearable Cardioverter Defibrillator (WCD) system, to wear until their ICD is implanted, or until their cardiac condition no longer puts them at high risk of SCA. A WCD system typically includes a support structure, such as a harness, vest, belt, or other garment that the patient is to wear. The WCD system further includes electronic components, such as a defibrillator and electrodes, coupled to the support structure. When the patient wears the WCD system, the electrodes make electrical contact with the patient's skin, and therefore can help sense the patient's electrocardiogram (ECG). If a shockable heart arrhythmia (e.g., ventricular fibrillation (VF) or ventricular tachycardia (VT)) is detected from the ECG, the defibrillator delivers an appropriate electric shock through the patient's body, and thus through the heart. The delivered shock may restart the patient's heart and thus save the patient's life. It should be understood that while WCD is used throughout the specification, the WCD may also be a wearable monitoring device (WMD), that is a wearable device without the ability to shock a patient. Unless otherwise specified, when the term "WCD" is used, it should be understood that this may also be a WMD, and vice versa.

In some cases, the user interface for changing and viewing parameters and patient information on a WCD is provided by an external companion device, such as a tablet or laptop computer, with a dedicated application. This application is a special purpose application that is compatible with the WCD and its programming as the communication interface changes, such as when new features are added to the WCD. The compatibility issue currently requires both a compatible version of the application as well as a tablet that can execute the compatible version of the application for the WMD to which it is connected. In addition, a custom application must be developed for each version of the WCD and for multiple potential companion devices. If the user does not have the latest application release, then they may not be able to program the WCD until the user upgrades the application, which may also include updating the tablet.

Accordingly, improved devices and methods for interfacing with a WMD using a companion device (such as a tablet) have eluded those skilled in the art, until now.

A wearable monitoring device system includes a wearable medical monitoring device (WMMD), including a support structure, a plurality of electrodes, a WMMD communication module, and a WMMD data store. The WMMD data store includes parameter data that define settings of the WMMD, interpreted code that provides access to the parameter data, a web server configured to serve the interpreted code. The WMMD includes a WMMD processor configured to execute the web server, the web server being operative to transmit the interpreted code over the WMMD communication module, modify the parameter data based on input received by the web server over the WMMD communication module. The system includes a companion device communicatively coupled to the WMMD, including a display, a companion communication module configured to communicatively couple the companion device and the WMMD, and a companion data store in which reside components, including. The companion data store includes a browser configured to render the interpreted code, the interpreted code defining a user interface that enables modification of the parameter data, the user interface being operative to receive input from a user of the companion device. A companion processor is included, configured to execute the browser, the browser being operative to receive the interpreted code over the companion communication module and to render the user interface on the display, receive input from the user, and return the input over the companion communication module to the WMMD communication module.

In another aspect, a wearable cardioverter defibrillator system includes a wearable cardioverter defibrillator (WCD). The WCD includes a support structure configured to be worn by a patient, a plurality of electrodes coupled to or integrated in the support structure, an energy storage module configured to store an electrical charge, a discharge circuit configured to be coupled to the energy storage module and configured to deliver one or more shocks to the patient while the support structure is worn by the patient using the plurality of electrodes and electrical charge stored in the energy storage module, and a WCD communication module. The WCD further includes data store in which resides components. The components include parameter data that define settings of the WMD, interpreted code that provides access to the parameter data, and a web server configured to serve up interpreted code. A user interface is implemented by interpreted code, a WMD communication module, and a WMD processor. The WCD further includes a WCD processor configured to transmit the interpreted code from the web server over the WCD communication module and modify the parameter data based on input received over the WCD communication module. The WCD system further includes a companion device communicatively coupled to the WCD. The companion device includes a display, a companion communication module configured to communicatively couple the companion device and the WCD. The companion device further includes a browser component configured to render the interpreted code, and to receive input from a user of the companion device, and a companion processor. The companion processor is configured to receive the interpreted code over the companion communication module, present the interpreted code to the browser component, receive input from the browser, and return the input over the companion communication module to the WCD communication module. When the web server transmits the interpreted code to the companion device, the browser component renders the interpreted code on the display of the companion device, and user input received by the browser component is returned to the WCD through the WCD communication module and the companion communication module.

None of the subject matter discussed in this section is necessarily prior art and may not be presumed to be prior art simply because it is presented in this section. Any reference to any prior art in this description is not, and should not be taken as, an acknowledgment or any form of suggestion that such prior art forms parts of the common general knowledge in any art in any country. Along these lines, any recognition of problems in the prior art discussed in this section or associated with such subject matter should not be treated as prior art, unless expressly stated to be prior art. Rather, the discussion of any subject matter in this section should be treated as part of the approach taken towards solving the particular problems identified. This approach in and of itself may also be inventive.

The summary provided above is intended to introduce a selection of concepts in a simplified form that are further described below in the Detailed Description. This summary is not intended to identify key features of the claimed subject matter, nor is it intended to be used as an aid in determining the scope of the claimed subject matter.

BRIEF DESCRIPTION OF THE DRAWINGS

FIG. 6 is a conceptual diagram of a security certificate (also referred to as a digital certificate) that may be used in various embodiments of the disclosure;

DETAILED DESCRIPTION

This disclosure is directed at systems and methods to expose a configuration interface of a WMD to a companion device without special purposed applications on the companion device.

While illustrative embodiments will be illustrated and described, it will be appreciated that various changes can be made therein without departing from the spirit and scope of the disclosure.

Figure 1:
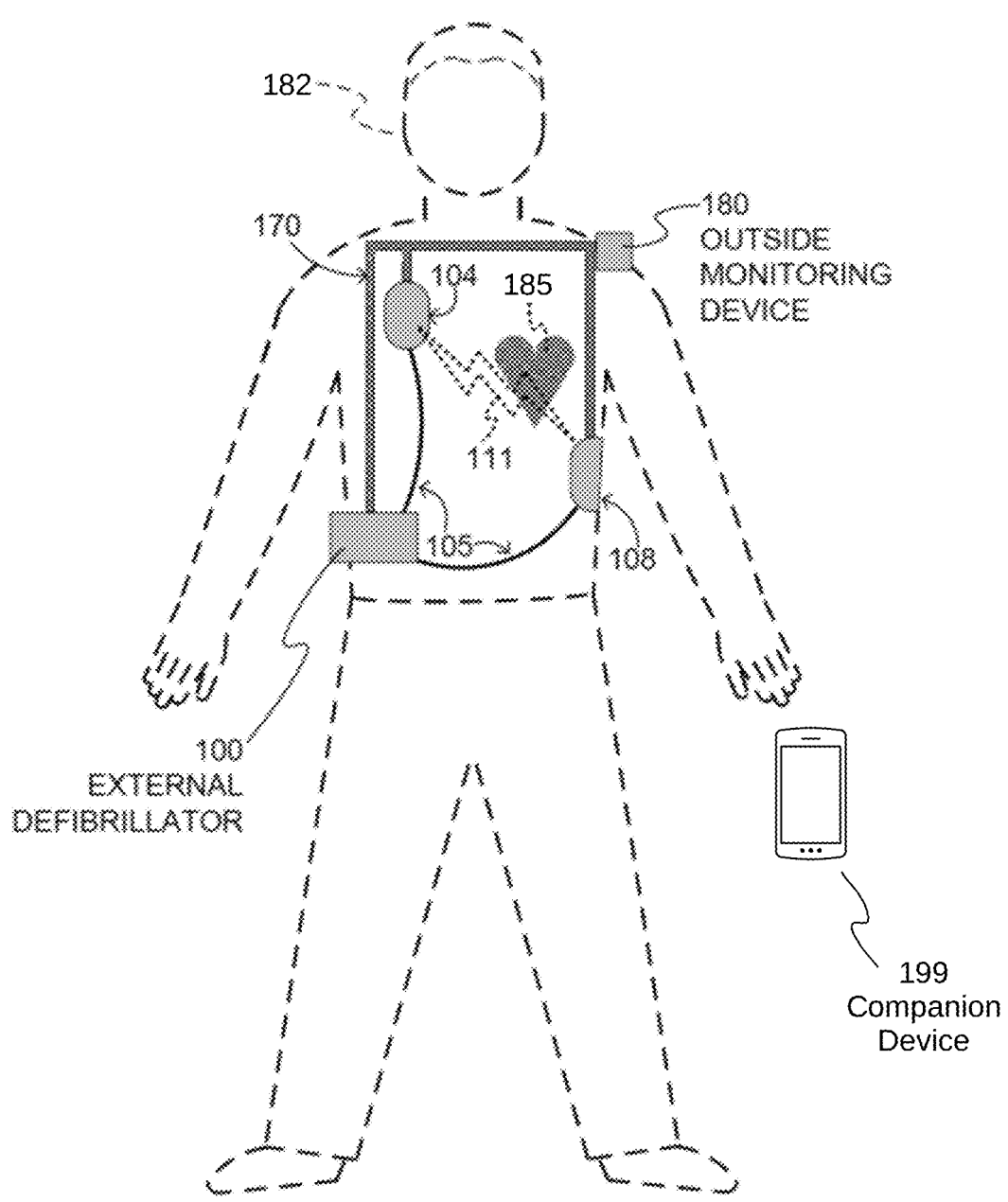
FIG. 1 is a conceptual diagram of a patient wearing an exemplary WCD, made according to embodiments.

Turning now to the drawings, FIG. 1 depicts a Wearable Cardioverter Defibrillator (WCD) system being worn by a patient 182, according to embodiments of the disclosure. The WCD described herein is presented as one example of a wearable monitoring device (WMD) that measures and captures cardiac data (e.g., ECG trace data) for a patient wearing the WCD system. In one instance, the WMD is a wearable medical monitoring device (WMMD). A WMMD should be understood a medical monitoring device subject to approval by a federal agency, such as the FDA, for use in medical applications.

Patient 182 may also be referred to as a person and/or wearer since the patient is wearing components of the WCD system. As shown, patient 182 is ambulatory, which means that while wearing the wearable portion of the WCD system under ordinary circumstances, patient 182 can walk around and is not necessarily bed ridden. While patient 182 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander or a manufacturer of the WCD. The particular context of these and other related terms within this description should be interpreted accordingly.

A WCD system according to embodiments can be configured to defibrillate the patient who is wearing the designated parts of the WCD system. Defibrillating can be by the WCD system delivering an electrical charge to the patient's body in the form of an electric shock. The electric shock can be delivered in one or more pulses and/or again should the WCD continue to detect a shockable rhythm. In alternative embodiments implemented as a WMD, the WCD system may monitor, for example, a patient's cardio output, but not deliver an electrical shock to the patient's body.

FIG. 1 also depicts components of a WCD system made according to embodiments.

One such component is a support structure 170 that is wearable by ambulatory patient 182. Accordingly, support structure 170 is configured to be worn by ambulatory patient 182 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 182 in a number of ways. For instance, defibrillator 100 and defibrillation electrodes 104, 108 can be coupled to support structure 170, directly or indirectly. In other words, support structure 170 can be configured to be worn by ambulatory patient 182 so as to maintain at least one of electrodes 104, 108 on the body of ambulatory patient 182, while patient 182 is moving around, etc. The electrode can be thus maintained on the body by being attached to the skin of patient 182, simply pressed against the skin directly or through garments, etc. In some embodiments the electrode is not necessarily pressed against the skin but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 182, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 185, in an effort to save the life of patient 182. Pulse 111 can further include one or more pacing pulses of lesser magnitude to simply pace heart 185 if needed, and so on.

Defibrillators typically decide whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 182. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 182, or a parameter of the WCD system, or a parameter of the environment, as will be described later in this document.

For some of these parameters, monitoring device 180 may include one or more sensors or transducers. Each one of such sensors can be configured to sense a parameter of patient 182, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 182 are also referred to herein as physiological inputs and patient inputs. In embodiments, a sensor can be construed more broadly, as encompassing many individual sensors.

Optionally, monitoring device 180 is physically coupled to support structure 170. In addition, monitoring device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 182. This customization may include a number of aspects. For instance, support structure 170 can be fitted to the body of patient 182. For another instance, baseline physiological parameters of patient 182 can be measured, such as the heart rate of patient 182 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

WCD system may further include a "companion" device 199. In various embodiments, the companion device 199 may be implemented as a mobile medical device that also includes various sensors for capturing patient parameters and/or environmental parameters. For example, the companion device 199 may include motion detection sensors, accelerometers, gyroscopic sensors, GPS location sensors, and the like. In still other embodiments, the companion device 199 may also include ECG monitoring components which interface directly with ECG electrodes. The companion device 199 further includes a user interface that enables the patient 182 to provide input to and receive output from the companion device 199.

In an embodiment, the companion device 199 is in communication with either the external defibrillator 100, the outside monitoring device 180 (if present), or both. Similarly, the companion device 199 may be in wireless communication with remote computing systems over a local or wide area network. For example, in various embodiments the companion device 199 may be implemented as a special purpose mobile communication device or as a downloadable app that may be installed on a cellular smartphone, or the like.

Figure 2:
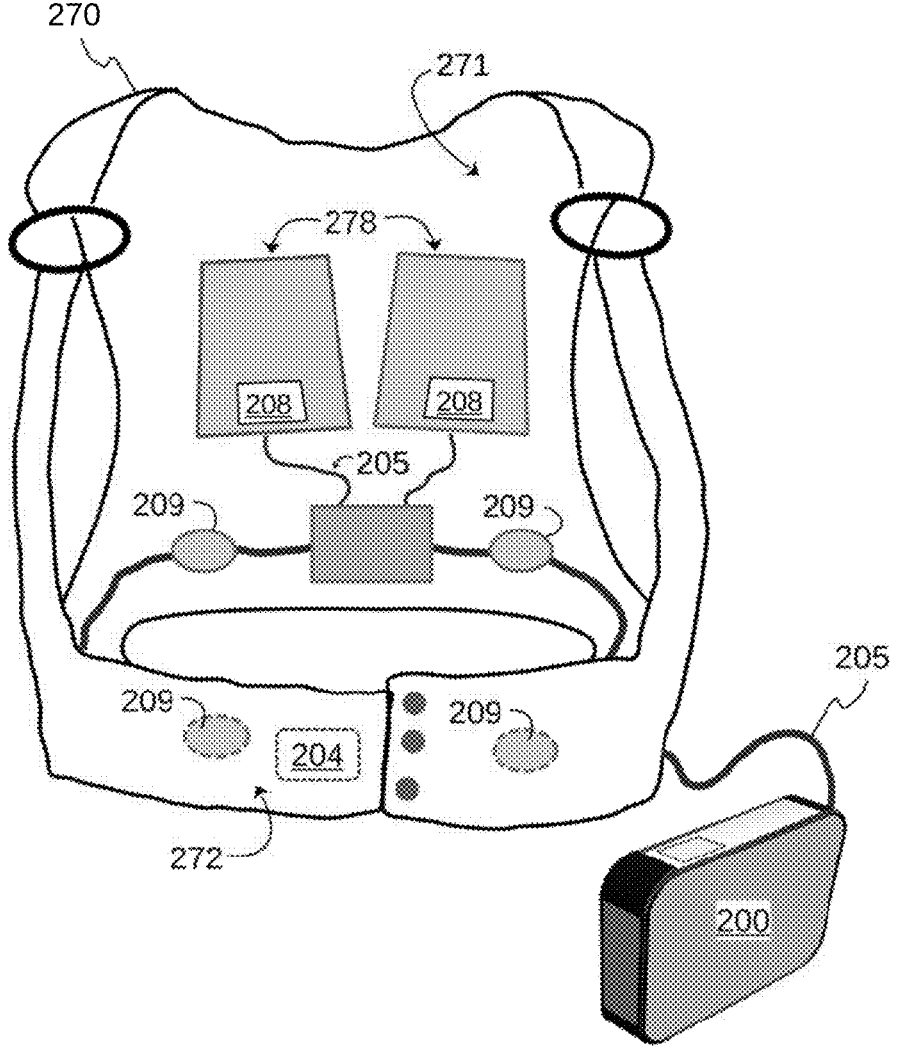
FIG. 2 is a conceptual diagram of sample embodiments of components of a WCD system made in accordance with this disclosure.

FIG. 2 is a conceptual diagram of components of an illustrative WCD system that may implement embodiments of the disclosure. As shown, a support structure 270 includes a vest-like wearable garment. Support structure 270 has a back side 271, and a front side 272 that closes in front of the chest of the patient.

The WCD system of FIG. 2 also includes an external defibrillator 200. FIG. 2 does not show support for external defibrillator 200, which may be carried in a purse, on a belt, by a strap over the shoulder, and so on. Wires 205 connect external defibrillator 200 to electrodes 204, 208, 209. Of those, electrodes 204, 208 are defibrillation electrodes, and electrodes 209 are ECG sensing electrodes. The electrodes shown on the front side 272 of the support structure 270 are illustrated in dashed line to represent that those electrodes are within the support structure 270 so that the electrodes may contact the patient.

Support structure 270 is configured to be worn by the ambulatory patient so as to maintain electrodes 204, 208, 209 in contact with the body of the patient. Back defibrillation electrodes 208 may be maintained in pockets of the support structure 270. Of course, the inside of pockets 278 can be made with conductive fabric, so that electrodes 208 can contact the back of the patient, especially with the help of conductive fluid that may be deployed. In addition, sensing electrodes 209 are maintained in positions that surround the patient's torso, for sensing ECG signals and/or the impedance of the patient.

Figure 3:
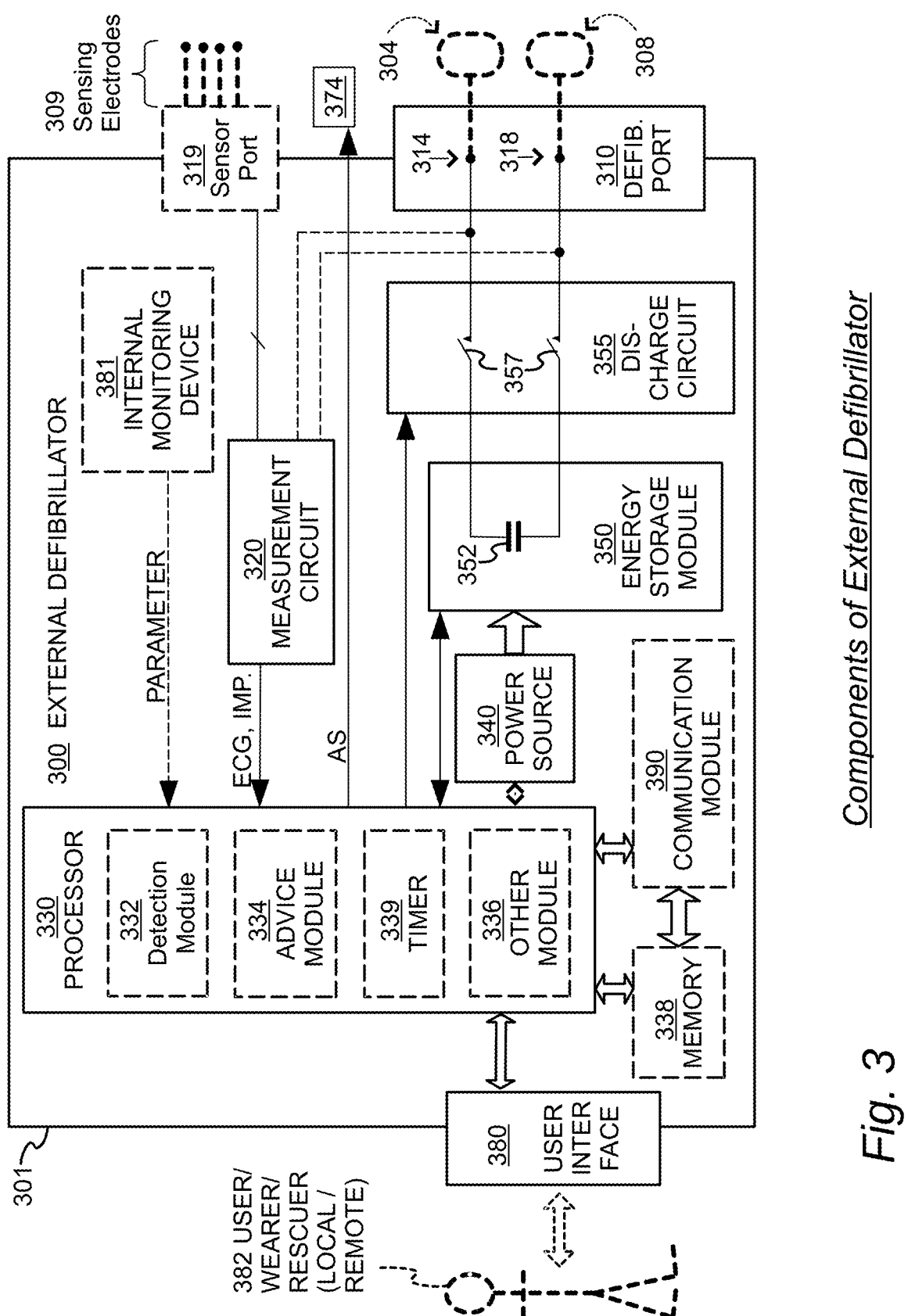
FIG. 3 is a functional diagram showing components of an illustrative external defibrillator made according to embodiments.

FIG. 3 is a diagram showing certain components of an illustrative external defibrillator 300, made according to embodiments. These components can be, for example, included in external defibrillator 100 of FIG. 1 and external defibrillator 200 of FIG. 2. External defibrillator 300 is intended for a patient who would be wearing it, such as ambulatory patient 182 of FIG. 1. The components shown in FIG. 3 are illustrative, and additional components not shown may, of course, be included.

The components shown in FIG. 3 can be provided in a housing 301, which may also be referred to as a casing. Defibrillator 300 may further include a user interface 380 for a user 382. User 382 can be patient 182, also known as wearer 182. Alternatively, user 382 can be a local rescuer at the scene, such as a bystander who might offer assistance, or a trained person. Or user 382 might be a remotely located trained caregiver in communication with the WCD system.

User interface 380 can be made in a number of ways. User interface 380 may include output devices, which can be visual, audible, or tactile, for communicating to a user by outputting images, sounds or vibrations. Images, sounds, vibrations, and anything that can be perceived by user 382 can also be called human-perceptible indications (HPIs). There are many examples of output devices. For example, an output device can be a light, or a screen to display what is sensed, detected and/or measured, and provide visual feedback to rescuer 382 for their resuscitation attempts, and so on. Another output device can be a speaker, which can be configured to issue voice prompts, beeps, loud alarm sounds and/or words to warn bystanders, etc.

User interface 380 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 300 may include an internal monitoring device 381. Device 381 is called an "internal" device because it is incorporated within housing 301. Monitoring device 381 can sense or monitor patient parameters such as patient physiological parameters, system parameters and/or environmental parameters, all of which can be called patient data. In other words, internal monitoring device 381 can be complementary or an alternative to outside monitoring device 180 of FIG. 1. Allocating which of the parameters are to be monitored by which of monitoring devices 180, 381 can be done according to design considerations. Device 381 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of patient parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 381 may include one or more sensors (described below) configured to acquire patient physiological signals.

Patient state parameters include recorded aspects of patient 382, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

In some embodiments, a trend may be detected in a monitored physiological parameter of patient 382. A trend can be detected by comparing values of parameters at different times over short and long terms. Parameters whose detected trends can particularly help include: (a) cardiac function (e.g., ejection fraction, stroke volume, cardiac output, etc.); (b) heart rate variability at rest or during exercise; (c) heart rate profile during exercise and measurement of activity vigor, such as from the profile of an accelerometer signal and informed from adaptive rate pacemaker technology; (d) heart rate trending; (e) perfusion, such as from $SpO_2$, $CO_2$, or other parameters such as those mentioned above, (f) respiratory function, respiratory rate, etc.; (g) motion, level of activity; and so on. Once a trend is detected, it can be stored and/or reported via a communication link, along perhaps with a warning if warranted. From the report, a physician monitoring the progress of patient 382 will know about a condition that is either not improving or deteriorating.

A WCD system made according to embodiments may include a motion detector. In embodiments, a motion detector can be implemented within monitoring device 180 or monitoring device 381. Such a motion detector can be made in many ways as is known in the art, for example by using an accelerometer. In this example, a motion detector 387 is implemented within monitoring device 381. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 381 includes a GPS location sensor as per the above, and if it is presumed that the patient is wearing the WCD system.

Defibrillator 300 typically includes a defibrillation port 310, which can be a socket in housing 301. Defibrillation port 310 includes electrical nodes 314, 318. Leads of defibrillation electrodes 304, 308, such as leads 105 of FIG. 1, can be plugged into defibrillation port 310, so as to make electrical contact with nodes 314, 318, respectively. It is also possible that defibrillation electrodes 304, 308 are connected continuously to defibrillation port 310, instead. Either way, defibrillation port 310 can be used for guiding, via electrodes, to the wearer at least some of the electrical charge that has been stored in an energy storage module 350 that is described more fully later in this document. The electric charge will be the shock for defibrillation, pacing, and so on.

Defibrillator 300 may optionally also have a sensor port 319 in housing 301. Commonly, but not exclusively, the sensor port 319 may be implemented as an ECG port. Sensor port 319 can be adapted for plugging in sensing electrodes 309, which may include ECG electrodes and ECG leads. It is also possible that sensing electrodes 309 can be connected continuously to sensor port 319, instead. If implemented as ECG electrodes, sensing electrodes 309 may be transducers that can help sense an ECG signal, e.g., a 12-lead signal, or a signal from a different number of leads, especially if they make good electrical contact with the body of the patient and in particular with the skin of the patient. As with defibrillation electrodes 304, 308, the support structure can be configured to be worn by patient 382 so as to maintain sensing electrodes 309 on a body of patient 382. For example, sensing electrodes 309 can be attached to the inside of support structure 170 for making good electrical contact with the patient, similarly with defibrillation electrodes 304, 308.

Many alternative sensing electrodes 309 are also envisioned. For example, sensing electrodes 309 may further include a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors.

In some embodiments, defibrillator 300 also includes a measurement circuit 320, as one or more of its working together with its sensors or transducers. Measurement circuit 320 senses one or more electrical physiological signals of the patient from sensor port 319, if provided. Even if defibrillator 300 lacks sensor port 319, measurement circuit 320 may optionally obtain physiological signals through nodes 314, 318 instead, when defibrillation electrodes 304, 308 are attached to the patient. In these cases, the input reflects an ECG measurement. The patient parameter can be an ECG, which can be sensed as a voltage difference between electrodes 304, 308. In addition, the patient parameter can be an impedance, which can be sensed between electrodes 304, 308 and/or between the connections of sensor port 319 considered pairwise. Sensing the impedance can be useful for detecting, among other things, whether these electrodes 304, 308 and/or sensing electrodes 309 are not making good electrical contact with the patient's body. These patient physiological signals may be sensed when available. Measurement circuit 320 can then render or generate information about them as inputs, data, other signals, etc. As such, measurement circuit 320 can be configured to render a patient input responsive to a patient parameter sensed by a sensor. In some embodiments, measurement circuit 320 can be configured to render a patient input, such as values of an ECG signal, responsive to the ECG signal sensed by sensing electrodes 309. More strictly speaking, the information rendered by measurement circuit 320 is output from it, but this information can be called an input because it is received as an input by a subsequent device or functionality.

Defibrillator 300 also includes a processor 330 (also referred to as WMD processor 330 or WCD processor 330). Processor 330 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include, or have access to, a non-transitory storage medium, such as memory 338 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 330 can be considered to have a number of modules. One such module can be a detection module 332. Detection module 332 can include a Ventricular Fibrillation (VF) detector. The patient's sensed ECG from measurement circuit 320, which can be available as inputs, data that reflect values, or values of other signals, may be used by the VF detector to determine whether the patient is experiencing VF. Detecting VF is useful because VF typically results in SCA. Detection module 332 can also include a Ventricular Tachycardia (VT) detector, and so on.

Another such module in processor 330 can be an advice module 334, which generates advice for what to do. The advice can be based on outputs of detection module 332. There can be many types of advice according to embodiments. In some embodiments, the advice is a shock/no shock determination that processor 330 can make, for example via advice module 334. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018, and since published as US 2019/0030351 A1, and also in U.S. patent application Ser. No. 16/038,007, filed on Jul. 17, 2018, and since published as US 2019/0030352 A1, both by the same applicant and incorporated herein by reference.

Processor 330 can include additional modules, such as other module 336, for other functions. For example, one instance of other module 336 may be a web server, such as described below in conjunction with FIG. 4. In addition, if internal monitoring device 381 is indeed provided, processor 330 may receive its inputs, etc.

Defibrillator 300 optionally further includes a memory 338, for use by the processor 330 in conjunction with executing the several executable modules. Memory 338 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 338 is thus a non-transitory storage medium. Memory 338, if provided, can include programs for processor 330, which processor 330 may be able to read and execute. More particularly, the programs can include sets of instructions in the form of code, which processor 330 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 330 and can also include protocols and ways that decisions can be made by advice module 334. In addition, memory 338 can store prompts for user 382 if this user is a local rescuer. Moreover, memory 338 can store data. This data can include patient data, system data, and environmental data, for example as learned by internal monitoring device 381 and outside monitoring device 180. The data can be stored in memory 338 before it is transmitted out of defibrillator 300 or be stored there after it is received by defibrillator 300.

Defibrillator 300 can optionally include a communication module 390, for establishing one or more wired or wireless communication links with other devices of other entities, such as a mobile companion device, a remote assistance center, Emergency Medical Services (EMS), and so on. The communication links can be used to transfer data and commands. The data may be patient data, event information, therapy attempted, CPR performance, system data, environmental data, and so on. For example, communication module 390 may transmit wirelessly, e.g., on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Communication module 390 may also include such interconnected sub-components as may be deemed necessary by a person skilled in the art, for example an antenna, portions of a processor, supporting electronics, outlet for a telephone or a network cable, etc.

Defibrillator 300 may also include a power source 340. To enable portability of defibrillator 300, power source 340 typically includes a battery. Such a battery is typically implemented as a battery pack, which can be rechargeable or not. Sometimes a combination is used of rechargeable and non-rechargeable battery packs. Other embodiments of power source 340 can include an AC power override, for where AC power will be available, an energy-storing capacitor, and so on. Appropriate components may be included to provide for charging or replacing power source 340. In some embodiments, power source 340 is controlled and/or monitored by processor 330.

Defibrillator 300 may additionally include an energy storage module 350. Energy storage module 350 can be coupled to the support structure of the WCD system, for example either directly or via the electrodes and their leads. Module 350 is where some electrical energy can be stored temporarily in the form of an electrical charge, when preparing it for discharge to administer a shock. In embodiments, module 350 can be charged from power source 340 to the desired amount of energy, as controlled by processor 330. In typical implementations, module 350 includes a capacitor 352, which can be a single capacitor or a system of capacitors, and so on. In some embodiments, energy storage module 350 includes a device that exhibits high power density, such as an ultracapacitor. As described above, capacitor 352 can store the energy in the form of an electrical charge, for delivering to the patient.

A decision to shock can be made responsive to the shock criterion being met. When the decision is to shock, processor 330 can be configured to cause at least some or all of the electrical charge stored in module 350 to be discharged through patient 182 while the support structure is worn by patient 182, so as to deliver a shock 111 to patient 182. For causing the discharge, defibrillator 300 moreover includes a discharge circuit 355. When the decision is to shock, processor 330 can be configured to control discharge circuit 355 to discharge through the patient at least some of all of the electrical charge stored in energy storage module 350. Discharging can be to nodes 314, 318, and from there to defibrillation electrodes 304, 308, so as to cause a shock to be delivered to the patient. Circuit 355 can include one or more switches 357. Switches 357 can be made in a number of ways, such as by an H-bridge, and so on. Circuit 355 could also be thus controlled via processor 330, and/or user interface 380. A time waveform of the discharge may be controlled by thus controlling discharge circuit 355. The amount of energy of the discharge can be controlled by how much energy storage module has been charged, and also by how long discharge circuit 355 is controlled to remain open.

Optionally, a WCD system according to embodiments also includes a fluid that it can deploy automatically between the defibrillation electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for defibrillation electrodes 304, 308, and/or for sensing electrodes 309.

The fluid may be initially stored in a fluid reservoir, not shown in FIG. 3. Such a fluid reservoir can be coupled to the support structure. In addition, a WCD system according to embodiments further includes a fluid deploying mechanism 374. Fluid deploying mechanism 374 can be configured to cause at least some of the fluid to be released from the reservoir and be deployed near one or both of the patient locations to which electrodes 304, 308 are configured to be attached to the patient. In some embodiments, fluid deploying mechanism 374 is activated prior to the electrical discharge responsive to receiving activation signal AS from a processor 330, which is described more fully later in this document.

Figure 4:
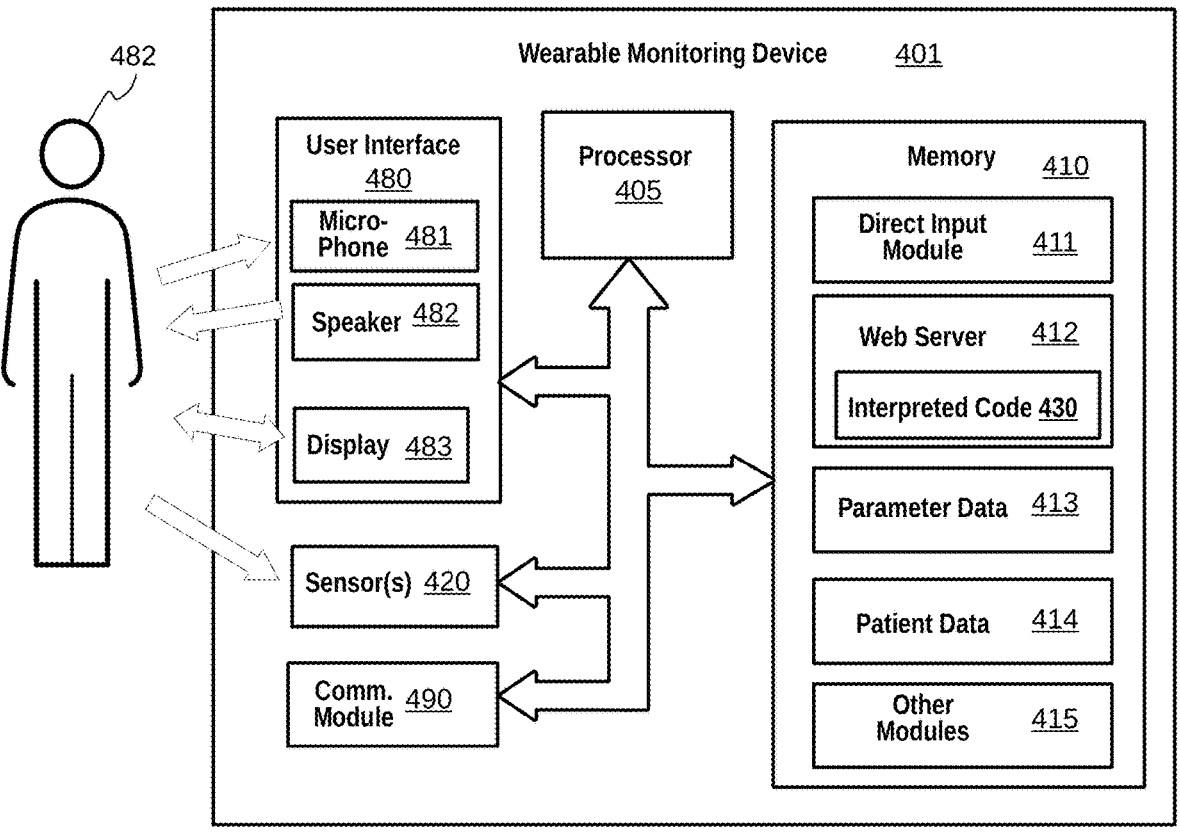
FIG. 4 is a functional diagram showing components of an illustrative mobile medical device made according to embodiments.

FIG. 4 is a functional block diagram generally illustrating a wearable monitoring device (WMD) 401 used in implementations of the disclosure. In some embodiments, WMD 401 may be implemented within or as part of the external defibrillator of a WCD system (e.g., external defibrillator 100, 200, or 300). Alternatively, the WMD 401 may be implemented within or as part of a standalone WMD (e.g., outside monitoring device 180). In another alternative, the WMD 401 may be implemented within or as part of a mobile companion device (e.g., companion device 199). Although illustrated in FIG. 4 as a unitary design, it will be appreciated that one or more of the functional blocks illustrated in FIG. 4 may, in various embodiments, be implemented within one or more other devices which are together incorporated into a WCD system.

The WMD 401 shown in FIG. 4 is illustrated, functionally, using a basic computing architecture that includes a processor 405 (also referred to as a WMD processor 405 or a WDC processor 405), a memory 410, and a bus 412 that connects the processor 405 to the memory 410. In various embodiments, the processor 405 may be implemented as any form of instruction processing unit, such as a Central Processing Unit (CPU), a Graphics Processing Unit (GPU), a Data Processing Unit (DPU), Accelerated Processing Unit (APU), Tensor Processing Unit (TPU), or the like.

A user interface 480 is also included and is a logical component that includes features to enable a user (e.g., patient 482) to provide input to and receive output from the WMD 401. In various embodiments, the user interface 480 receives manual input from the patient (e.g., keystrokes or taps). For example, the user interface 480 may include a microphone 481 to receive sounds and convert those sounds into computer-usable signals. The user interface 480 may also include a speaker 482 to convert computer-usable signals into sounds that may be heard. The user interface 480 may also include a visual display 483 to convert computer-usable signals into visual data that may be visually perceived. In some embodiments, the visual display 483 is a touchscreen display that may also receive tactile input in the form of touches on the visual display 483.

One or more sensors 420 may also be included in the WMD 401 for sensing physiological signals of the patient. As with the external defibrillator 300 shown in FIG. 3 and described above, the sensors 420 may include any one or more components used to detect various parameters (e.g., patient parameters, system parameters, environmental parameters, or the like). For instance, in some embodiments where the WMD 401 is implemented as part of an external defibrillator (e.g., external defibrillator 300) or external monitoring device (e.g., outside monitoring device 180), the sensors may include any or all of the sensors described above. In some embodiments where the WMD 401 is implemented within or as part of a companion device 199, the sensors may omit those used to capture patient parameters (e.g., ECG electrodes) and instead include only sensors used to detect environmental parameters (e.g., motion detector, accelerometer, compass, proximity sensor, barometer, or the like). It will be appreciated that in some embodiments, if the WMD 401 is implemented within a companion device 199, it could rely on sensor data collected by either or both of the external defibrillator or the outside monitoring device. In such embodiments, most or even all of the sensors 409 could be omitted from or unused by the WMD 401 itself. Still further, duplicative sensors (e.g., between the external defibrillator and the WMD 401) are also possible.

A communication module 490 is also included in the WMD 401 to enable communication between the WMD 401 and other devices (such as companion device 199). In various embodiments, the communication module 490 may implement wired and/or wireless communication between the WMD 401 and an external defibrillator. For example, if the WMD 401 is implemented within a companion device (e.g., companion device 199), the communication module may enable bidirectional communication between the companion device 199 and the external defibrillator 100. In this way, the WMD 401 may receive signals from the external defibrillator 100, such as ECG waveforms and other patient parameters detected by the external defibrillator 100. Similarly, the WMD 401 may transmit instructions and/or data to the external defibrillator 100, such as a request for the external defibrillator 100 to transmit information to the WMD 401. Still further, the communication module 490 may implement cellular communications functionality to enable long-range cellular data communications with remote computing devices. These and other embodiments of the communication module 490 will be apparent to those skilled in the art.

The memory 410 is a data store implemented within the WMD 401 to store software components, such as data and various executable modules. The memory 410 may be implemented as volatile, non-volatile, or a combination of volatile and non-volatile memory. Non-volatile memory may be used to persistently store information, and volatile memory may be used by the processor 405 while executing various instructions. Accordingly, the term "memory" as used herein should be given its broadest interpretation as any repository in which computer-readable information may be held temporarily and/or permanently.

Within the memory 410 are several executable modules according to various embodiments. For example, a direct input module 411 may be included to receive and process direct user data provided by external sources. In one example, the direct input module 411 is configured to prompt the patient 482 for and accept data through the user interface 480, either through the microphone, the display, the speaker or any combination thereof. The direct input module 411 may be configured to receive user-provided data and combine that data with other data, such as parameter data 413 and/or patient data 414. For example, the patient 482 may be prompted to provide certain information by speaking to the microphone 481. Similarly, the patient 482 may be presented with choices that may be selected on the display 483. These are but a few examples of direct patient input.

In accordance with some embodiments, a web server 412 is included within the memory. In some embodiments, the web server 412 is software that uses HTTP (Hypertext Transfer Protocol) and/or other protocols to respond to client requests made over a wide area network by returning interpreted-page content. Besides HTTP, the web server 412 may also support IP (the Internet Protocol), HTTPS (Secure Hypertext Transfer Protocol), FTP (File Transfer Protocol) protocols, and other communication protocols.

In operation, the web server 412 communicates with a client (e.g., a web browser) using the Secure Hypertext Transfer Protocol (HTTPS). The web server 412 provides interpreted code 430, which in some embodiments is Hypertext Markup Language (HTML). The content (or code) can be static (for example, text and images) or dynamic (for example, assembled "on the fly"). To deliver dynamic content, in some embodiments, the web server 412 supports server-side scripting languages to encode business logic into the communication. In some embodiments, these languages may include any one or more of Active Server Pages (ASP), Java, JavaScript, PHP, Python, Ruby, and the like.

In some embodiments, the interpreted code 430 provides the requesting client with access to parameter data of the WMD as described herein. In some embodiments, the interpreted code 430 provides access to patient data. In some embodiments, the patient data includes a patient identifier, a number of shocks delivered, a run report record, a WMD status, a heart rhythm, or the like. In some embodiments, the interpreted code 430 is implemented as HTML. In some embodiments, the interpreted code 430 may also include cascading style sheets (CSS). In operation, the processor 405 transmits the interpreted code 430 from the web server 412 over the communication module 490 to a requesting client. In such embodiments, browser software executing on the client can then modify parameter data through one or more inputs received via the display 480 or, perhaps, from a companion device (such as companion device 199). The one or more inputs can then be transmitted back to the web server through the communication module 490.

In some embodiments, the interpreted code 430 provides the requesting client with access to parameter data 413 of the WMD and/or patient data 414 as described herein. Examples of the parameter data 413 include volume levels for notifications, display settings, localization settings (e.g., language, text direction, or the like), battery power profiles, patient configuration information, device configuration information, or the like. Examples of the patient data 414 include any information pertaining to the patient 482, such as a patient identifier, a number of shocks delivered, a run report record, a WMD status, a heart rhythm, or the like. In some embodiments, the interpreted code 430 implements a web interface that provides access to the parameter data 413 and/or the patient data 414. In some embodiments, the interpreted code 430 is implemented as HTML. In some embodiments, the interpreted code 430 may also include CSS.

In operation, the processor 405 transmits the interpreted code 430 from the web server 412 over the communication module 490 to a requesting client. In such embodiments, browser software executing on the requesting client interprets the interpreted code 430 and renders the code on a display. In that way, by using browser software on the requesting client (e.g., companion device 199), the user can remotely modify parameter data 413 through one or more inputs received from the browser software. In various embodiments, the browser software may render the interpreted code 430 locally, such as on display 480. In other embodiments, browser software may render the interpreted code 430 on a remote device, such as companion device 199. The one or more inputs can then be transmitted back to the web server 412 through the communication module 490.

In some embodiments, the WCD further comprises patient data 414, the web server's interpreted code is further configured to provide access to the patient data, and the companion browser is further configured to display the patient data. In some embodiments, the patient information comprises at least a patient identifier, a number of shocks delivered, a run report record, a WCD status, or a presented heart rhythm. In some embodiments, patient data may be patient parameters as described herein. For example, Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of patient parameters include the patient's ECG, blood oxygen level, blood flow, blood pressure, blood perfusion, pulsatile change in light transmission or reflection properties of perfused tissue, heart sounds, heart wall motion, breathing sounds and pulse. In some embodiments, the WCD may include one or more sensors as described herein configured to acquire patient physiological signals.

Patient state parameters include recorded aspects of patient 382, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

In some embodiments, the web server transmits the interpreted code to the companion device, the browser component renders the interpreted code on the display of the companion device, and user input received by the browser component is returned to the WCD through the WCD communication module and the companion communication module. In some embodiments, such as when the interpreted code includes patient data, a user of the WCD may change the patient data displayed by the browser component through a series of inputs (e.g., taps, keystrokes, button presses, or the like) on the communication device. The communication device may then return the inputs to the WCD through the companion communication module. The WCD processor may then change the patient data in the interpreted code served by the web server.

As discussed, the various components illustrated for convenience within WMD 480 may alternatively be implemented within or distributed across other devices. For example, in other embodiments the user interface 480 may be implemented in a companion mobile device (not shown) rather than in the WMD 480. In such an embodiment, the WMD 480 may employ the communication module 490 to communicate patient parameters and/or sensed data to the companion mobile device. Many other permutations will be apparent to those skilled in the art.

Figure 5:
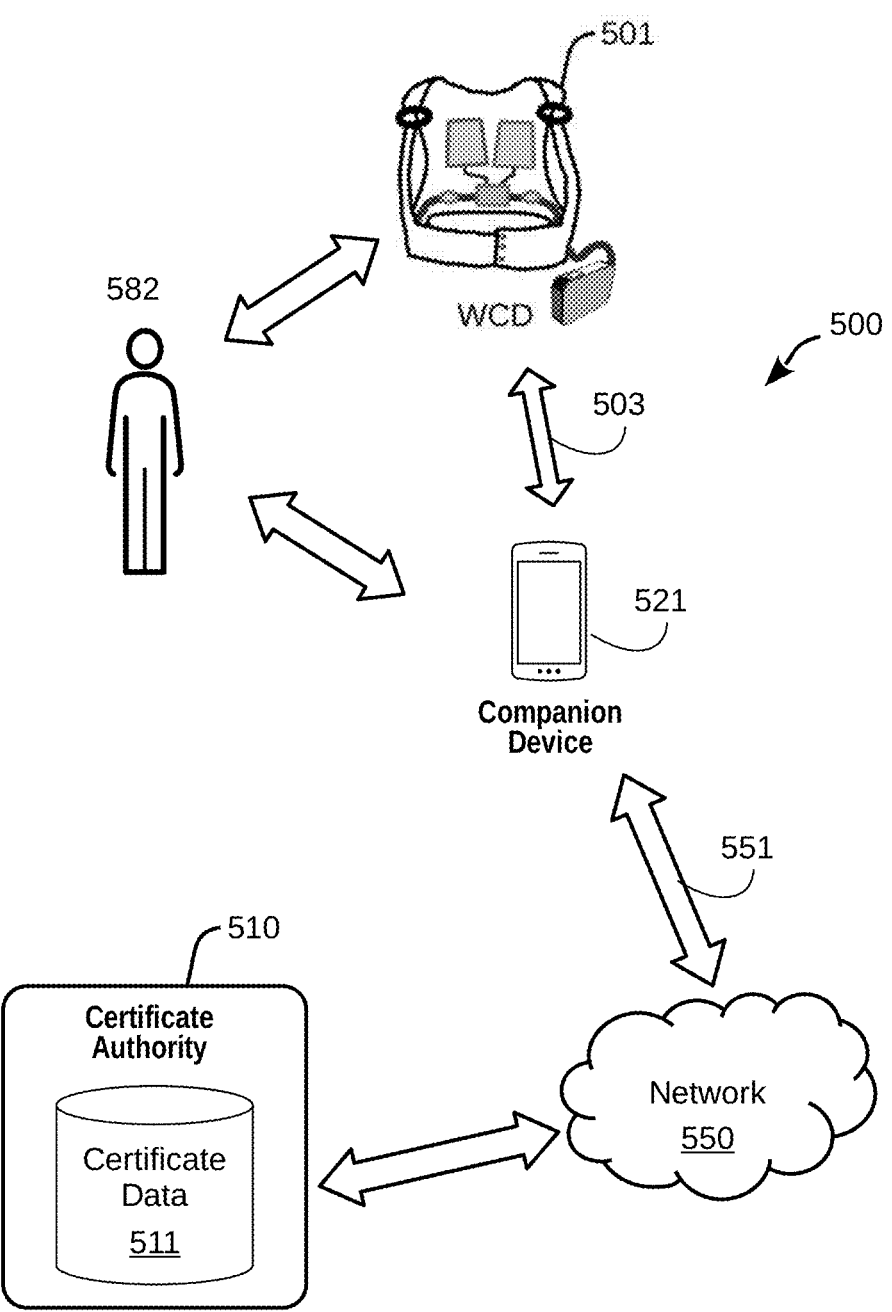
FIG. 5 is a conceptual diagram generally illustrating a health monitoring environment according to embodiments.

FIG. 5 is a conceptual diagram generally illustrating a health monitoring environment 500 according to embodiments. As illustrated in FIG. 5, the health monitoring environment 500 includes a wearable cardiac monitoring device (WCD 501), a mobile device (e.g., companion device) 521, and a remote patient data platform (CareStation server 510). Each of those components variously communicates with one or more of the others either locally over a local communication link or remotely over a remote communication link through a wide area network 550, such as the Internet. While the companion device 521 is illustrated as a mobile device, it should be understood that the companion device 521 may take any number of forms, including a tablet, a laptop, a desktop computer, a smart phone, or the like.

The wearable cardiac monitoring device 501 may be any medical device configured to detect and report on patient physiological parameters, such as described at length above. The wearable cardiac monitoring device 501 is described herein as a WCD for simplicity of discussion only. One example of such a WCD is the Assure WCD developed and offered by Kestra Medical Technologies, Inc. of Kirkland, Washington. Many other types of wearable cardiac monitoring devices may be used in various alternative embodiments without departing from the spirit of the disclosure. Accordingly, reference to use of a WCD as the cardiac monitoring device 501 is illustrative only and is not limiting of the disclosure.

The WCD 501 may also communicate over a local communication link 503 with a mobile device 521 operating an app configured to facilitate communication between the patient 582, the WCD 501, and other remote devices. In various embodiments, the mobile device 521 may be referred to as a companion device. In one example, the mobile device 521 and the WCD 501 may communicate using a relatively short-range local communication link 503, such as Ethernet, Bluetooth low energy (BLE), or Wi-Fi. In some embodiments, the mobile device 521 and the WCD 501 may communicate using a wired connection, personal area network (PAN), or local area network (LAN) connection. The mobile device 521 may also communicate with other remote devices using a remote communication link 551 to a wide area network 550, such as the Internet. In one specific embodiment, the application operating on the mobile device 521 may be the Assure patient app developed and offered by Kestra Medical Technologies, Inc. of Kirkland, Washington. In various embodiments, the patient application operating on the mobile device 521 may provide a graphical user interface (GUI) that enables review of patient physiological parameters captured by the WCD 501.

In some embodiments, the remote patient data platform (CareStation server 510) is implemented as a remote server for use by medical professionals and/or clinicians that offers efficient tools for managing cardiac patient care. In various embodiments, the remote patient data platform delivers relevant data and valuable insights into patient heart rhythms and usage compliance by providing clear patient reports that include VT, VF, bradycardia, asystole, and non-sustained ventricular arrhythmia episodes; WCD usage and physical activity trends; and may include a population dashboard with configurable notifications. One example of such a remote patient data platform is the CareStation platform developed and offered by Kestra Medical Technologies, Inc. of Kirkland, Washington. The remote patient data platform is described herein as a CareStation server for simplicity of discussion only. Many other types of remote patient data platforms may be used in various alternative embodiments without departing from the spirit of the disclosure. Accordingly, reference to use of a CareStation server as the remote patient data platform is illustrative only and is not limiting of the disclosure.

In some embodiments, the CareStation server 510 operates as a certificate authority. In such embodiments, the certificate authority acts as a trusted organization to issues signed digital certificates and to attest to the authenticity of those signed digital certificates. Certificate Authorities are known in the art.

Generally stated, patient data is collected by the WCD 501 and uploaded, either by the WCD 501 directly or by using an associated mobile device (e.g., companion device 521), to the CareStation server 510. In addition, the mobile device 521 may also collect some forms of patient data.

The CareStation server 510 stores the patient data and may perform several analyses on the patient data to identify patient health issues, such as the occurrence of arrythmias, shockable and non-shockable events, and other medical events. In addition, after-action evaluations may be performed on the patient data to help improve the quality of future shock therapy.

In some embodiments, such as described in conjunction with FIG. 4, the WCD 501 may include a web server (such as web server 412). In some embodiments, the WCD 501 may be communicatively coupled to the companion device 521. The WCD 501 may include a processor configured to transmit interpreted code from the web server over a communication module and modify the parameter data based on input received over the communication module. The interpreted code may be transmitted to a companion device communication module. In some embodiments, the companion device includes a display and a browser module. In some embodiments, the companion device is configured to receive the interpreted code over the companion communication module, present the interpreted code to the browser component, receive input from the browser, and return the input over the companion communication module to the WMD communication module.

In some embodiments, the WMD further comprises patient data, the user interface of the web server is further configured to provide access to the patient data, and the companion browser is further configured to display the patient data. In some embodiments, the patient information may take any number of many different forms, such as a patient identifier, a number of shocks delivered, a run report record, a WCD status, a heart rhythm, or the like.

Authenticating Embodiments

In one embodiment, the web server includes one or more security measures configured to restrict access to a non-authorized user to the web server. In some embodiments, the one or more security measures restrict access to one or more features of, or even complete access to the web server depending on authorization credentials of the user. For example, various authorized users may have varying need for access to the different features made available by the web server. For instance, the patient would have a need for access to different information than a health care professional, a caretaker, or a manufacturer of the WCD, and vice versa In some embodiments, the web server comprises one or more security measures configured to restrict access to a non-authorized user to the web server. In some embodiments, the one or more security measures restrict one or more features of the web server depending on an identity of the authorized user. In some embodiments, the identity of the authorized user is selected from the patient, a health care professional, a caretaker, or a manufacturer of the WCD.

In some embodiments, the one or more security measures are a set of authorization credentials, such as a username and a password. In some embodiments, the set of authorization credentials may be further protected with two-factor authentication. In such embodiments, an authorized user may receive a set of credentials specific to the identity of the authorized user. For example, a patient may receive a patient set of credentials that allows the patient to view the status of the WMD and WCD and patient information but may restrict the patient from adjusting parameters of the WCD or WMD. In some embodiments, a medical professional may receive a set of medical professional credentials that allows the medical professional to adjust the parameters of the WCD or WMD, review patient information, and view the status of the WMD or WCD. Additionally, for example, a manufacturer may receive a set of manufacturer credentials that allows it to adjust the parameters of the WCD or WMD, but not access patient information.

In alternative embodiments, the one or more security measures include security certificates. FIG. 6 is a conceptual diagram of a security certificate 600 (also referred to as a digital certificate) that may be used in various embodiments of the disclosure. In certain embodiments, the security certificate 600 is a digital file that includes various fields of data. Those fields may include one or more of a subject, an issuer, an expiration, an algorithm, and a unique identifier. All of these fields need not be included in every embodiment, and other fields may also be included which are not described here. These fields are provided as illustrative only.

The subject field may identify the certificate holder or the entity with whom the security certificate 600 is associated. The certificate holder may be an individual, an organization, a specific computing device, or any entity whose identity has been verified and whose trust is being attested to by a certifying authority (as explained in conjunction with FIG. 7-8).

The issuer field may identify a trusted Certificate Authority who may be trusted to verify the authenticity of entities. In one example, an Assure Certificate Authority may be established and trusted to verify the identity of various components that are authorized to communicate with, for example, a WCD or other components of a WCD system.

An expiration field may identify a date after which the security certificate is no longer valid or can no longer be used to trust the subject. In some embodiments, a "not before" field may also be included to identify a date before which the security certificate is not valid.

A public key portion of the security certificate is included to provide a public key for the subject and related public key information. Public/private key pairs are used in Public Key Infrastructure (PKI) systems to facilitate asymmetric cryptography. The public key information may include further information that describes the public key, such as the algorithm (e.g., Elliptic Curve Public Key), the key size (e.g., 256 bits), and the key usage (e.g. can encrypt, verify, derive). The public key portion of the security certificate 501 enables recipients of the security certificate 501 to communicate securely with the subject through encrypted communication sessions.

An algorithm field may be included in the security certificate 501 to specify a particular algorithm that was used to sign the certificate as described below. Examples of algorithms which may be used include SHA-1, SHA-2, SHA-256, and the like.

A unique identifier or serial number is also included to uniquely identify the security certificate. Note that the unique identifier should be distinguished from the subject in that the subject identifies the trusted entity or the entity with which the security certificate is associated whereas the unique identifier identifies the actual security certificate itself.

Optionally, one or more permissions fields may be included in the security certificate 600. In some embodiments, certain elements of the WCD System (such as the WCD) need to govern what operations other connected components are allowed to perform while in communication. For example, in some embodiments the WCD may be configured to allow a limited set of element types to change critical configuration parameters of the WCD but to prevent other element types from doing so. An example of this may be that the WCD can be configured to allow a Tablet to configure such parameters, but it doesn't allow a companion device to do so. In such embodiments, one or more fields of the security certificate 600 (collectively referred to as the "permissions" field for simplicity of discussion)

Other data fields may also be included and used for various reasons. Arbitrary or structured data may be included to provide or convey any manner of information deemed worthy of trust or having a need to ensure its integrity.

A signature is also included with the security certificate 600. The signature is a data structure that represents an attestation to the authenticity of the security certificate 600. The signature is created by the issuer (e.g., the Certificate Authority) and is verifiable using a security certificate (or digital certificate) of the issuer. Although the signature may be created in different ways, one example may be that the body of the security certificate is input to the algorithm (e.g., a hashing algorithm) identified within the security certificate together with a private key of the issuer. The algorithm creates a unique value based on the body of the security certificate and the issuer's private key. The issuer's public key can then be used by the identified algorithm to verify that the body of the security certificate has not been changed since the signature was created by the issuer. In this way, the integrity of the data in the body of the security certificate can be trusted so long as the issuer is trusted.

Figure 7:
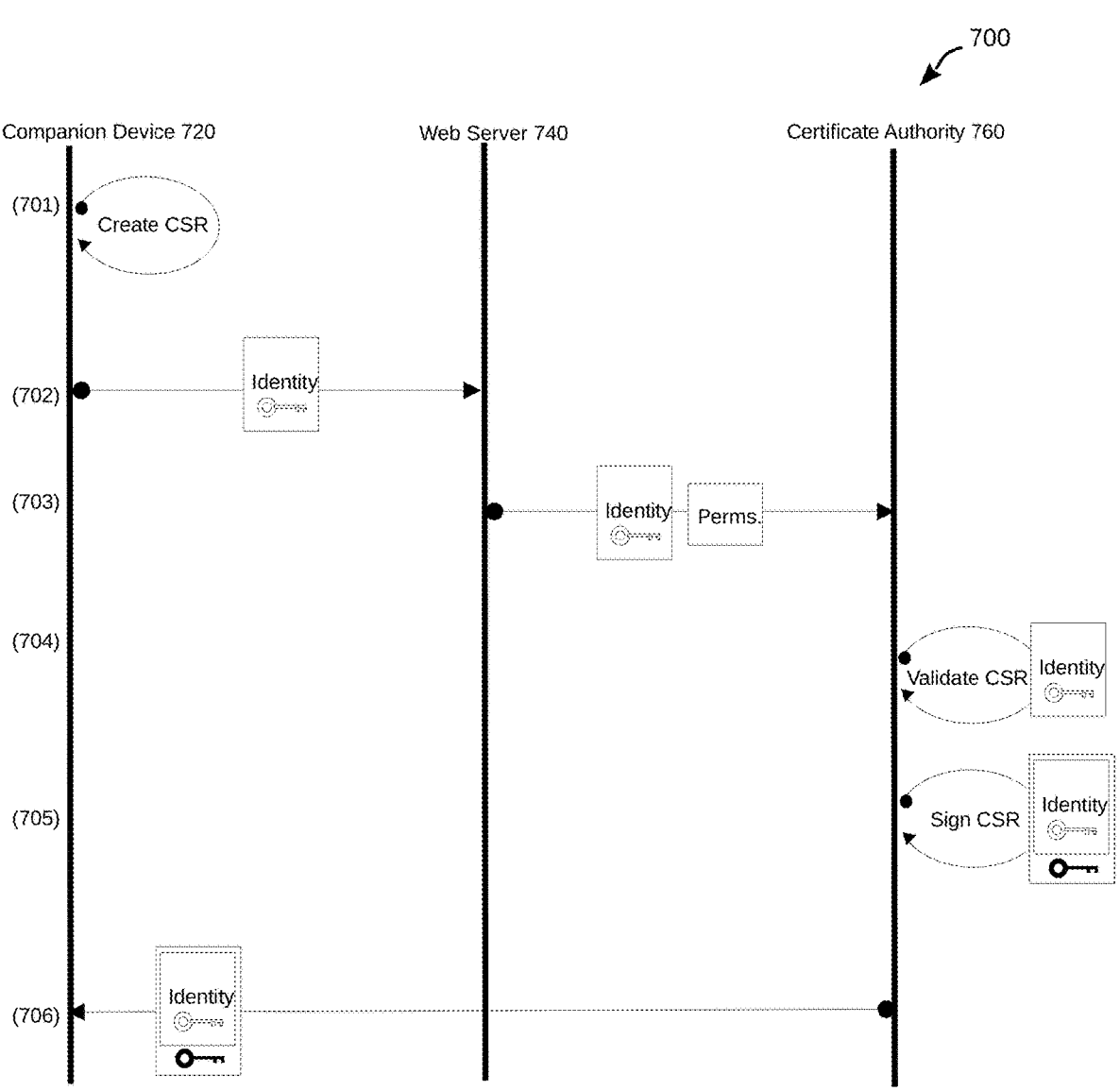
FIG. 7 is a functional flow diagram generally illustrating a process for creation of a security certificate in accordance with this disclosure.
Figure 8:
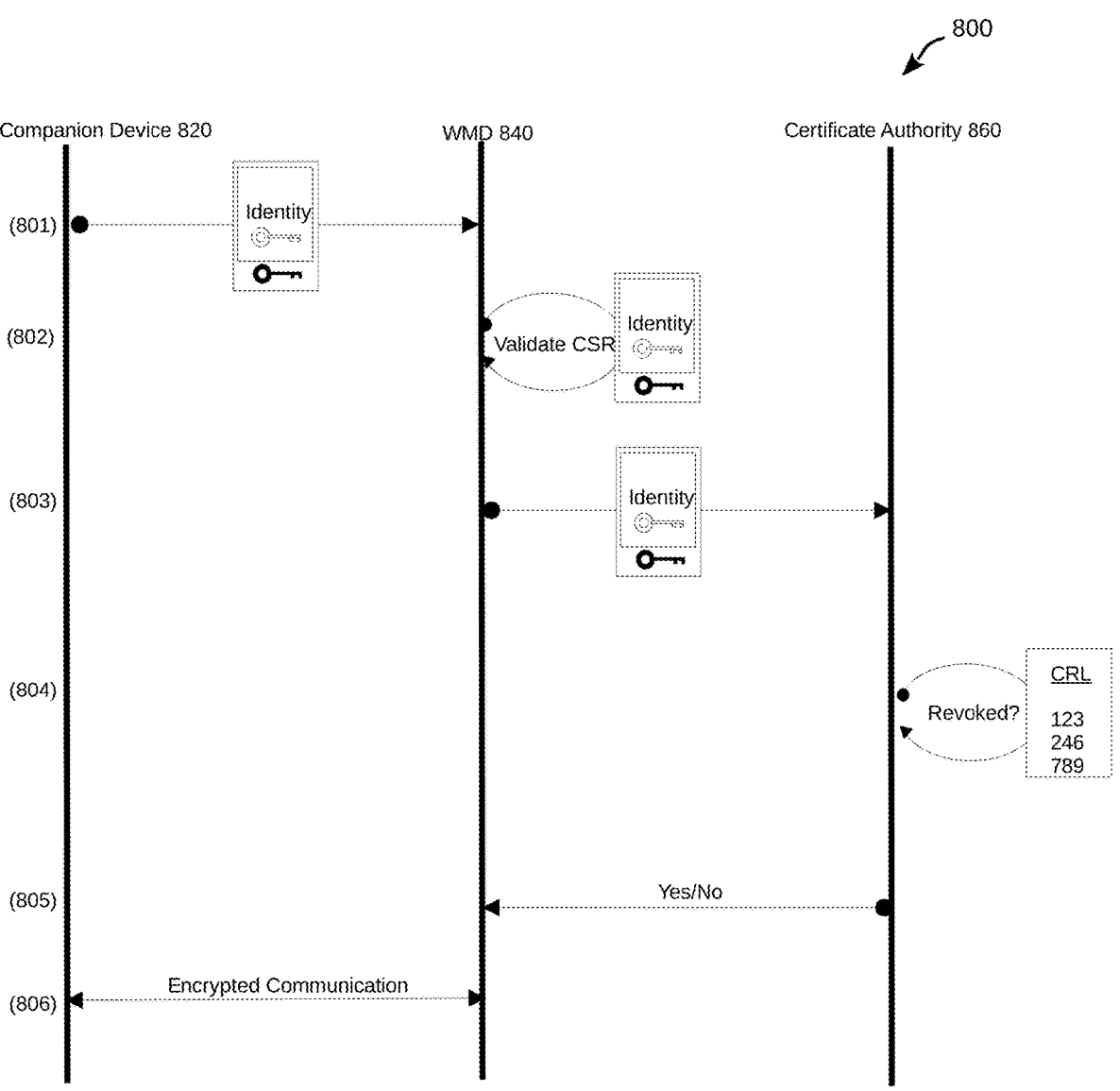
FIG. 8 illustrates a process for using security certificates within a WCD system to ensure trusted communications and proper access between components of the WCD system in accordance with this disclosure.

Turning now to FIGS. 7 and 8, the operation of embodiments of the disclosure will be described with reference to the components shown in FIGS. 1 through 6 and described above. Although the following operations are provided for completeness of the disclosure, it will be appreciated that deviations from these operations are envisioned, and this description should not be viewed as limiting of the scope of the disclosure.

FIG. 7 is a functional flow diagram generally illustrating a process 700 for creation of a security certificate in accordance with this disclosure. The certificate creation process 700 may be implemented by components of the WCD system 301 illustrated in FIG. 3 and described above. Alternatively, other components may be modified or adapted to implement the several steps discussed here. Reference to components of the same name is for simplicity of discussion only, and the steps may be performed by various components.

The process 700 begins (701) when a companion device, (Companion Device 720) creates a Certificate Signing Request (CSR) for a "requesting element" (not shown) that desires to communicate with a WCD. As part of that operation, the Companion Device 720 may create a public/private key pair on behalf of the requesting element, or the public/private key pair may be provided to the Companion Device 720 by the requesting element. The CSR includes information that identifies the requesting element and includes the public key for the requesting element.

Once the CSR is created, the Companion Device 720 transmits (702) the CSR to a component that is responsible for facilitating the creation of security certificates for use in the WCD system. In this example, a Web Server 740 is that responsible component. Accordingly, the Companion Device 720 transmits the CSR to the Web Server 740. It will be appreciated that, to ensure the CSR is securely delivered to the Web Server 740, the Companion Device 740 may first establish a secure connection to the Web Server 740 using the Companion Device's own security certificate.

The Web Server 740 forwards (703) the CSR to the Certificate Authority 760. In certain embodiments, the Web Server 740 may forward additional information along with the CSR. For example, the Web Server 740 may maintain records about what components are authorized to perform which functions on or in conjunction with a WCD. In such an embodiment, the Web Server 740 may forward permission information along with the CSR to the Certificate Authority 760.

The Certificate Authority 760 is configured to perform operations to validate (704) the accuracy of information contained within the CSR. For example, the Certificate Authority 760 may have access to records or data that can establish that the CSR did in fact originate with the requesting element and properly names the requesting element. Still further, the Certificate Authority 760 may have access to records or data that confirm the requesting element is authorized access to other components within the WCD system, such as the WCD itself. Even further, the Certificate Authority 760 may have information that either confirms permission information provided by the Web Server 740 (if such information was provided) or describes appropriate permissions for the requesting element in the first instance. In one embodiment, the certifying authority may be on the Care Station Server (as shown in FIG. 5).

If the CSR survives validation, then the Certificate Authority 760 creates a security certificate including the information from the CSR and signs that security certificate using the private key of the Certificate Authority 760. By signing the certificate, the Certificate Authority is both securing the information within the certificate against tampering and attesting to the validity of that information.

With the security certificate signed, the Certificate Authority and Web Server 740 return the signed certificate to the Companion Device 720, which then installs the security certificate on the requesting element. In that way, the requesting element (i.e., the companion device) may now authenticate itself to and have secure communications with the WCD, for example.

It should be noted that although both are referred to as a "web server", the Web Server 740 illustrated in FIG. 7 need not be the same as the web server implemented within the subject WMD (e.g., web server 412). Any appropriate web server may be used in the process 700 illustrated in FIG. 7 to create a security certificate, and the web server used in process 700 need not provide access to any features or settings stored on a WMD.

FIG. 8 illustrates a process 800 for using security certificates within a WCD system to ensure trusted communications and proper access between components of the WCD system. Again, although described here in the context of a WCD, the teachings apply equally to any WMD. The certificate use process 800 may be implemented by components of the WCD system as described above. Alternatively, other components may be modified or adapted to implement the several steps discussed here. Reference to components of the same name is for simplicity of discussion only, and the steps may be performed by various components.

The process 800 begins (801) when a companion device 820 desires to initiate communications with another component within a WCD system. The other component is a web server of the WCD 840 in this example, but it could be any other component within the WCD system. In accordance with the disclosure, the companion device 820 initiates a handshake with the WCD 840 to exchange security certificates. During this process, the companion device 820 sends its security certificate to the WCD 840, and the WCD 840 returns its own security certificate (not shown).

With the security certificate in hand, the WCD 840 performs steps (802) to validate the security certificate. For instance, the WCD 840 may identify the Certificate Authority from information within the security certificate to determine if the security certificate is attested to by a trusted Certificate Authority. Once identified, the WCD 840 checks a certificate store to determine if the identified Certificate Authority is trusted by the WCD 840. If so, the WCD 840 uses a stored security certificate (the CA Certificate) to verify the integrity of the received security certificate. In short, the WCD 840 uses the CA Certificate to verify the authenticity of the security certificate and that its contents have not been tampered with. The WCD 840 also ensures that the security certificate is within the proper timeframe for its use (e.g., it is currently in effect and has not yet expired).

In an optional step (803), the WCD 840 (or other receiving component) may perform a check to ensure that the security certificate has not been revoked since it was issued. In one embodiment, the WCD 840 transmits the security certificate (or a portion thereof, such as the serial number) to another component, such as the Certificate Authority 860, for verification.

In such an embodiment, the Certificate Authority 860 would compare (804) the received security certificate against a Certificate Revocation List (CRL) to determine if the security certificate has been revoked. The Certificate Authority 860 would then return (805) a pass/fail or yes/no response to indicate whether the security certificate had been revoked.

In an alternative embodiment, rather than transmit the security certificate, the WCD 840 may request (803) the CRL from the Certificate Authority 860, which would then return (805 the CRL to the WCD 840 so that the WCD 840 can itself determine if the security certificate has been revoked. In such an embodiment, the WCD 840 could cache the CRL for future use to reduce the number of network communications it performs for the purpose of certificate verification.

If the security certificate is adequately verified and confirmed, the WCD 840 may then allow a communication session (806) with the companion device 820. In addition, through the exchange of security certificates and, hence, public keys, the communication session may be encrypted between the two components to ensure that the data exchanged is not compromised. However, if the security certificate fails any of the tests, the WCD 840 prohibits communication with the trusted component 820 (which now becomes untrusted). In various embodiments, when the WCD 840 initiates the secure connection, it may use the security certificate, and specifically permission fields, to determine which operations the companion device 820 is allowed to perform. Although referred to generically as a permission field, it will be appreciated that the WCD 840 may use any data within the security certificate (such as an "element type" field) to control the extent of permission that is granted to the companion device 820. In other words, the security certificate may, but need not have a dedicated field that explicitly describes permissions. Operative permissions may be implied based on other data within the security certificate. For example, the security certificate may contain a device type field that describes the type of connecting element, such as Tablet, Companion Device, Manufacturing System, etc., and various permissions may be assigned to different device types. Another example is a region field that describes the geographical region for the trusted component, such as United States, European Union, Canada, Japan, etc. In such embodiments, the security certificate can be used to select an appropriate localization component (e.g., language, left-to-right text orientation, and the like).

Other embodiments include combinations and sub-combinations of features described or shown in the drawings herein, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A wearable monitoring device system, comprising:
a wearable medical monitoring device (WMMD), comprising:
a support structure configured to be worn by a patient;
a plurality of electrodes coupled to the support structure;
a WMMD communication module;
a WMMD data store, communicatively coupled to the WMMD communication module, configured to reside at least a web server configured to serve interpreted code, wherein the interpreted code provides access to parameter data indicative of settings of the WMMD; and
a WMMD processor configured to:
execute the web server, the web server being operative to transmit the interpreted code over the WMMD communication module; and
modify the parameter data based on input received by the web server over the WMMD communication module; and
a companion device communicatively coupled to the WMMD, including:
a display;
a companion communication module configured to communicatively couple the companion device and the WMMD;
a companion data store communicatively coupled to the companion communication module, the companion data store including a browser configured to render the interpreted code, received from the WMMD, on a user interface of the companion device that enables modification of the parameter data, based on the input received from a user of the companion device; and a companion processor configured to:
receive the interpreted code over the companion communication module and to render the user interface on the display; and
receive the input from the user,
wherein the web server transmits the interpreted code to the companion device, the browser renders the interpreted code on the display of the companion device, and wherein the input received from the user is returned to the WMMD over a communication link between the WMMD communication module and the companion communication module,
wherein the web server comprises one or more security measures to restrict access, based on one or more features of the interpreted code depending on a set of authorization credentials with two-factor authentication,
wherein the one or more security measures comprise one or more security certificates that reside as a digital file, and wherein the digital file comprises fields to verify authenticity of the one or more security certificates.

2. The wearable monitoring device system of claim 1, wherein the WMMD data store further includes patient data that defines parameters of the patient, and wherein the interpreted code further provides access to the patient data.

3. The wearable monitoring device system of claim 2, wherein the patient parameters comprise one or more of a patient identifier, a number of shocks delivered, a run report record, a WMMD status, or a heart rhythm.

4. The wearable monitoring device system of claim 1, wherein the set of authorization credentials is based on whether the user is the patient, a health care professional, or a manufacturer of the WMMD.

5. The wearable monitoring device system of claim 1, wherein the interpreted code is Hypertext Markup Language (HTML).

6. The wearable monitoring device system of claim 1, wherein the communication link is a Wi-Fi, Bluetooth low energy (BLE), wired connection, personal area network (PAN), or local area network (LAN) connection.

7. The wearable monitoring device system of claim 1, wherein the companion device is a tablet, a laptop, a desktop computer, or a smart phone.

8. The wearable monitoring device system of claim 1, wherein the interpreted code includes one or more accessibility features.

9. A wearable cardioverter defibrillator system, comprising:
a wearable cardioverter defibrillator (WCD) comprising:
a support structure configured to be worn by a patient;
a plurality of electrodes coupled to the support structure;
an energy storage module configured to store electrical charge;
a discharge circuit configured to be coupled to the energy storage module and configured to deliver one or more shocks to the patient while the support structure is worn by the patient using the plurality of electrodes and electrical charge stored in the energy storage module;
a WCD communication module;
a WCD data store, communicatively coupled to the WCD communication module, configured to reside at least a web server configured to serve interpreted code, wherein the interpreted code provides access to parameter data indicative of settings of the WCD; and
a WCD processor configured to:
execute the web server, the web server being operative to transmit the interpreted code over the WCD communication module; and modify the parameter data based on input received by the web server over the WCD communication module; and a companion device communicatively coupled to the WCD, including:

a display;

a companion communication module configured to communicatively couple the companion device and the WCD;

a companion data store, communicatively coupled to the companion communication module, the companion data store including:

a browser configured to render the interpreted code, received from the WCD, on a user interface of the companion device that enables modification of the parameter data, based on the input received from a user of the companion device; and a companion processor configured to:

receive the interpreted code over the companion communication module and to render the user interface on the display; and receive the input from the user, wherein the web server transmits the interpreted code to the companion device, the browser renders the interpreted code on the display of the companion device, and wherein the input received from the user is returned to the WCD over a communication link between the WCD communication module and the companion communication module, wherein the web server comprises one or more security measures to restrict access, based on one or more features of the interpreted code depending on a set of authorization credentials with two-factor authentication, wherein the one or more security measures comprise one or more security certificates that reside as a digital file, and wherein the digital file comprises fields to verify the authenticity of the one or more security certificates.

10. The wearable cardioverter defibrillator system of claim 9, wherein the WCD data store further includes patient data that defines parameters of the patient, and wherein the interpreted code further provides access to the patient data.

11. The wearable cardioverter defibrillator system of claim 10, wherein the patient parameters comprise one or more of a patient identifier, a number of shocks delivered, a run report record, a WCD status, or a heart rhythm.

12. The wearable cardioverter defibrillator system of claim 9, wherein the set of authorization credentials is based on whether a user is the patient, a health care professional, or a manufacturer of the WCD.

13. The wearable cardioverter defibrillator system of claim 9, wherein the interpreted code is Hypertext Markup Language (HTML).

14. The wearable cardioverter defibrillator system of claim 9, wherein the WCD and the companion device are communicatively coupled with a Wi-Fi, Bluetooth low energy (BLE), wired connection, personal area network (PAN), or local area network (LAN) connection.

15. The wearable cardioverter defibrillator system of claim 9, wherein the companion device is a tablet, a laptop, a desktop computer, or a smart phone.

16. The wearable cardioverter defibrillator system of claim 9, wherein the interpreted code includes one or more accessibility features.

* * * * *